United States Patent
Strommer et al.

(10) Patent No.: US 8,055,327 B2
(45) Date of Patent: *Nov. 8, 2011

(54) AUTOMATIC GUIDEWIRE MANEUVERING SYSTEM AND METHOD

(75) Inventors: Gera Strommer, Haifa (IL); Uzi Eichler, Haifa (IL); Lior Sobe, Raanana (IL)

(73) Assignee: MediGuide Ltd., Haifa (IL)

( * ) Notice: Subject to any disclaimer, the term of this patent is extended or adjusted under 35 U.S.C. 154(b) by 720 days.

This patent is subject to a terminal disclaimer.

(21) Appl. No.: 10/940,423

(22) Filed: Sep. 14, 2004

(65) Prior Publication Data

US 2005/0197566 A1    Sep. 8, 2005

Related U.S. Application Data

(63) Continuation-in-part of application No. 10/800,129, filed on Mar. 8, 2004, now Pat. No. 7,811,294.

(51) Int. Cl.
*A61B 5/05* (2006.01)

(52) U.S. Cl. ..................................... 600/424

(58) Field of Classification Search ................ 600/424, 600/103, 117
See application file for complete search history.

(56) References Cited

U.S. PATENT DOCUMENTS

| | | | |
|---|---|---|---|
| 4,794,931 A | | 1/1989 | Yock |
| 5,078,140 A | * | 1/1992 | Kwoh ........................... 600/417 |
| 5,271,400 A | | 12/1993 | Dumoulin et al. |
| 5,318,025 A | | 6/1994 | Dumoulin et al. |
| 5,492,131 A | | 2/1996 | Galel |
| 5,638,819 A | * | 6/1997 | Manwaring et al. .......... 600/424 |
| 5,681,260 A | | 10/1997 | Ueda et al. |
| 5,738,666 A | * | 4/1998 | Watson et al. ................ 604/264 |
| 5,873,822 A | * | 2/1999 | Ferre et al. .................... 600/407 |
| 5,951,571 A | * | 9/1999 | Audette ......................... 606/130 |
| 6,015,414 A | | 1/2000 | Werp et al. |
| 6,035,856 A | * | 3/2000 | LaFontaine et al. .......... 128/898 |
| 6,216,027 B1 | * | 4/2001 | Willis et al. ................... 600/424 |

(Continued)

FOREIGN PATENT DOCUMENTS

JP    2002328114    11/2002

(Continued)

OTHER PUBLICATIONS

Beyar, Dalia, "Remote Control Catheterization", WO 1999-45994 Sep. 16, 1999.

(Continued)

*Primary Examiner* — Tse Chen
*Assistant Examiner* — Elmer Chao
(74) *Attorney, Agent, or Firm* — Dykema Gossett PLLC

(57) ABSTRACT

Method for guiding a catheter within a lumen system of the body of a patient includes receiving consecutive position inputs from a user to guide the catheter in real time within the lumen system, determining a user defined position for the catheter tip determining continuously successive incremental paths along a trail defined by a plurality of user defined positions, and directing a moving mechanism to incrementally move the catheter within the lumen system along each of the incremental paths, each of the user defined positions being determined for each of the received consecutive position inputs, the successive incremental paths being determined between a real time catheter tip position and the adjacent proceeding user defined position, according to a topological representation of the lumen system, the moving mechanism being directed to incrementally move the catheter from each of a plurality of real time positions, toward the adjacent proceeding user defined position.

15 Claims, 4 Drawing Sheets

U.S. PATENT DOCUMENTS

| | | | |
|---|---|---|---|
| 6,216,029 B1 | 4/2001 | Paltieli | |
| 6,233,476 B1* | 5/2001 | Strommer et al. | 600/424 |
| 6,246,898 B1 | 6/2001 | Vesely et al. | |
| 6,259,943 B1* | 7/2001 | Cosman et al. | 600/429 |
| 6,288,785 B1* | 9/2001 | Frantz et al. | 356/614 |
| 6,304,769 B1* | 10/2001 | Arenson et al. | 600/424 |
| 6,314,310 B1* | 11/2001 | Ben-Haim et al. | 600/424 |
| 6,470,207 B1 | 10/2002 | Simon et al. | |
| 6,501,981 B1 | 12/2002 | Schweikard et al. | |
| 6,514,237 B1 | 2/2003 | Maseda | |
| 6,546,277 B1* | 4/2003 | Franck et al. | 600/426 |
| 6,594,517 B1* | 7/2003 | Nevo | 600/411 |
| 6,671,538 B1* | 12/2003 | Ehnholm et al. | 600/425 |
| 6,725,080 B2 | 4/2004 | Melkent et al. | |
| 6,860,878 B2 | 3/2005 | Brock | |
| 6,892,090 B2 | 5/2005 | Verard et al. | |
| 6,892,091 B1 | 5/2005 | Ben-Haim et al. | |
| 6,920,347 B2 | 7/2005 | Simon et al. | |
| 6,947,786 B2 | 9/2005 | Simon et al. | |
| 7,276,044 B2 | 10/2007 | Ferry et al. | |
| 7,811,294 B2 | 10/2010 | Strommer et al. | |
| 2001/0031919 A1 | 10/2001 | Strommer et al. | |
| 2002/0049375 A1* | 4/2002 | Strommer et al. | 600/407 |
| 2002/0103430 A1* | 8/2002 | Hastings et al. | 600/411 |
| 2002/0193686 A1 | 12/2002 | Gilboa | |
| 2003/0220557 A1* | 11/2003 | Cleary et al. | 600/409 |
| 2004/0024371 A1 | 2/2004 | Plicchi et al. | |
| 2004/0077942 A1 | 4/2004 | Hall et al. | |
| 2004/0097805 A1* | 5/2004 | Verard et al. | 600/428 |
| 2004/0254566 A1* | 12/2004 | Plicchi et al. | 606/1 |
| 2005/0107688 A1* | 5/2005 | Strommer | 600/424 |
| 2005/0197557 A1 | 9/2005 | Strommer et al. | |
| 2005/0197566 A1 | 9/2005 | Strommer et al. | |
| 2006/0058647 A1 | 3/2006 | Strommer et al. | |

FOREIGN PATENT DOCUMENTS

| | | |
|---|---|---|
| JP | 2003305032 | 10/2003 |
| WO | WO-00/16684 | 3/2000 |

OTHER PUBLICATIONS

Hastings, Roger N. et al., "Systems and methods for interventional medicine", WO 2003-086190 A1 Oct. 23, 2003.

Schaldach, Max et al., "Apparatus for the automatic performance of diagnostic and/or therapeutic actions in body cavites", 2002-0042570 A1, Apr. 11, 2002, Entire document.

"Supplementary Partial European Search Report", EP05709124.1-1526 May 4, 2009.

* cited by examiner

AUTOMATIC GUIDEWIRE MANEUVERING SYSTEM AND METHOD

CROSS-REFERENCE TO PRIOR APPLICATION

This is a continuation in part application of U.S. application Ser. No. 10/800,129 filed on Mar. 8, 2004.

FIELD OF THE DISCLOSED TECHNIQUE

The disclosed technique relates to medical equipment in general, and to methods and systems for maneuvering a catheter within a lumen of a body of a patient, in particular.

BACKGROUND OF THE DISCLOSED TECHNIQUE

Various diagnostic and medical operations on lumens of the body of a patient, such as the circulation system, the gastrointestinal tract, the brain vessels, the bronchial tree, and the like, are preformed by inserting a catheter through the lumen. Since the catheter is generally a bulky device, it is difficult to guide it to the operational site all on its own. For this purpose, a guidewire whose diameter is substantially smaller than that of the catheter, is inserted to the operational site before inserting the catheter, and then the catheter is passed over the guidewire and guided to the operational site.

Methods and systems for maneuvering the guidewire through the lumen to the operational site, are known in the art. Generally, the operator manipulates the movements of the guidewire, by manually pushing or pulling the guidewire or twisting the guidewire, while he watches an image of the tip of the guidewire, against a real time two-dimensional image of the lumen (e.g., by employing a fluoroscopy angiogram). In this manner, the tip of the guidewire is maneuvered at various bifurcations of the lumens, in order to reach the operational site. The same method is employed for manipulating a catheter, only that a marker (e.g., an X-ray opaque material) is located on the tip of the catheter.

U.S. Pat. No. 6,594,517 B1 issued to Nevo and entitled "Method and Apparatus for Generating Controlled Torques on Objects Particularly Objects Inside a Living Body", is directed to a system and method for applying a controlled torque on an intra-body device, to bend the tip of the intra-body device. The system includes an input device, a processing and control unit, and electronic interface, the intra-body device, a torque generating module, a location and direction module and a magnetic resonance imaging system (MRI). The MRI includes a computer, an image display, a gradient activation control unit, an MRI magnet, and a set of three orthogonal gradient coils. The torque generating module includes three micro-coils.

The processing and control unit is connected with the input device, the electronic interface, the computer, and with the gradient activation control unit. The torque generating module and the location and direction module are located at the tip of the intra-body device. The torque generating module and the location and direction module are connected with the electronic interface. The computer is connected with the image display and with the gradient activation control unit. The gradient activation control unit is connected with the orthogonal gradient coils.

The processing and control unit controls the electrical currents through the micro-coils, in order to cause the torque generating module to generate a resultant magnetic dipole to interact with the magnetic field produced by the MRI magnet. This interaction produces a torque of the desired direction and magnitude, in order to steer the tip of the intra-body device. The gradient activation control unit provides the processing and control unit, information respective of the electromagnetic gradient fields generated by the three orthogonal gradient coils, and the timing sequence of the activation of these coils. The image display provides a real time image of the operation field. The location and direction module provides the location and direction or orientation of the tip of the intra-body device. The computer provides the processing and control unit, the event schedule of the MRI system, to prevent image artifacts due to activation of the torque generating module, when the MRI magnets are activated for imaging.

A stereotaxis system is employed for steering a guidewire of a catheter through the lumen, and bending the tip of the guidewire, by applying a magnetic field to the guidewire through a plurality of magnets. Magnetic fields are applied to cause the guidewire to turn in different directions. U.S. Pat. No. 6,035,856 describes such a method.

U.S. Pat. No. 6,035,856 issued to LaFontaine et al., and entitled "Percutaneous Bypass with Branching Vessel", is directed to a method for performing a bypass on a first occlusion of a branching vessel of the aorta. A coronary artery which includes the first occlusion, and a branching vessel branch out of the aorta. A standard guide-catheter is advanced through the aorta up to the ostium of the branching vessel. An occlusion forming device is advanced through the guide-catheter into the branching vessel, to produce a second occlusion in the branching vessel. The occlusion device includes an elongate portion and a heated balloon.

The occlusion forming device is removed from the aorta through the guide-catheter and a cutting device is advanced through the guide-catheter proximal to the second occlusion. The cutting device includes an elongate member, a steerable guidewire, a proximal occlusion balloon, a distal balloon, a stent, a cutting blade, a first piece of magnetic material and a transmitter. The cutting blade is located distal to the distal balloon, the first piece of the magnetic material is located between the cutting blade and the distal balloon and the transmitter is located within the distal balloon. The distal balloon is located within the stent. The transmitter emits radio frequency signals.

The wall of the branching vessel is cut by employing the cutting blade. The distal balloon is kept in the expanded position, in order to occlude the branching vessel after the branching vessel has been cut. The severed end of the branching vessel is steered toward a region of the coronary artery distal to the first occlusion, by maneuvering the steerable guidewire or by manipulating the first piece of the magnetic material by a second piece of magnetic material, wherein the second piece of magnetic material is located outside the body of the patient.

The true position and the relative position of the transmitter and thus the position of the severed end of the branching vessel, is determined by employing a triangulation and coordinate mapping system. The triangulation and coordinate mapping system includes three reference electrodes which are located outside the body of the patient. Two of the reference electrodes are located on opposite sides of the heart and the third is located on the back. The three reference electrodes are used to triangulate on the transmitter.

When the severed end of the branching vessel is properly positioned, an aperture is formed in the coronary artery distal to the first occlusion, by employing the cutting blade. The severed end of the branching vessel is inserted into the coronary artery through the aperture and the stent is expanded by inflating the distal balloon, thereby attaching the severed end of the branching vessel to the lumen of the coronary artery.

SUMMARY OF THE DISCLOSED TECHNIQUE

It is an object of the disclosed technique to provide a novel method and system for using a feedback from a position sensor located on the tip of a wire (or a catheter), to automatically maneuver and guide the tip of the catheter to a predefined designated position based on a structural roadmap of the vessel tree.

In accordance with the disclosed technique, there is thus provided a method for guiding a catheter within a lumen system of the body of a patient. The method includes the procedures of receiving consecutive position inputs from a user, to guide the catheter in real time, within the lumen system, and determining a user defined position for the tip of the catheter, for each of the received consecutive position inputs.

The method further includes the procedures of constantly detecting the real time position of the tip of the catheter, and determining continuously successive incremental paths along a trail defined by the user defined positions, between the real time position and the adjacent proceeding user defined position, according to a topological representation of the lumen system. The method further includes the procedure of directing a moving mechanism to incrementally move the catheter within the lumen system along each of the incremental paths, from each of a plurality of real time positions, toward the adjacent proceeding user defined position.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a system which automatically controls the movements of a catheter to a desired location within a lumen of a patient, according to a path within the lumen and according to the current position of the tip of the catheter within the lumen, while employing the current position as a feedback to control the movement. The path which the tip of the catheter is to follow is preplanned and is determined at an imaging session prior to the operational session, by employing a dynamic imager. Alternatively, the system maneuvers the catheter within the lumen, to the desired location, according to the circulation map of the body of the patient. The operator can override the automatic operation of the system and revert to the manual mode at any time, while observing a representation of the tip of the catheter against a real time two-dimensional image of the lumen. An organ monitor, such as an electrocardiogram (ECG) for monitoring an organ timing signal of an organ can be employed with the system, to display the two-dimensional image, as well as the three-dimensional structural model of the vessel tree by taking into account the movements of the lumen caused by pulsations of the organ (e.g., the heart).

The term "catheter" herein below, refers to an elongated body which can be inserted to a lumen of the body of a patient. The catheter can be for example, a guidewire for guiding a medical device to a certain location within the lumen, and the like. The term "topological representation" herein below, refers to a mapping of a lumen system (e.g., the circulation, the bronchial tree, the urogenital system, the renal system) of the body of the patient, which a system according to the disclosed technique employs, in order to maneuver the catheter from an origin to a destination. The mapping can be either two-dimensional or three-dimensional. Alternatively, it is noted that the term "topological representation" may include just the path to be followed in the lumen system. The term "position" herein below, refers either to the location, to the orientation or both the location and the orientation, of an object in a three-dimensional coordinate system.

Figure 1:
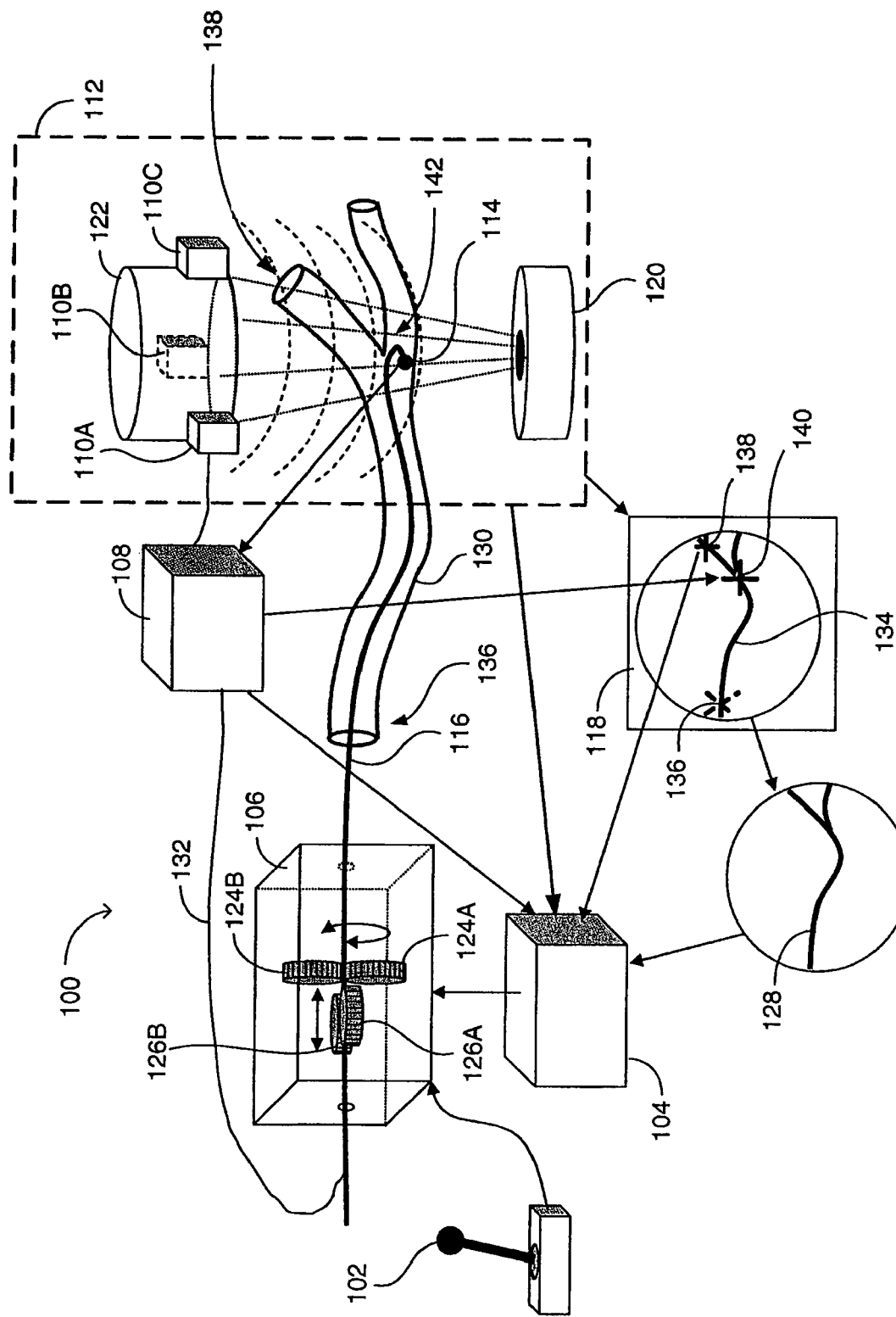
FIG. 1 is a schematic illustration of a system for automatically maneuvering a catheter within a lumen of the body of a patient, constructed and operative in accordance with an embodiment of the disclosed technique.
Figure 2:
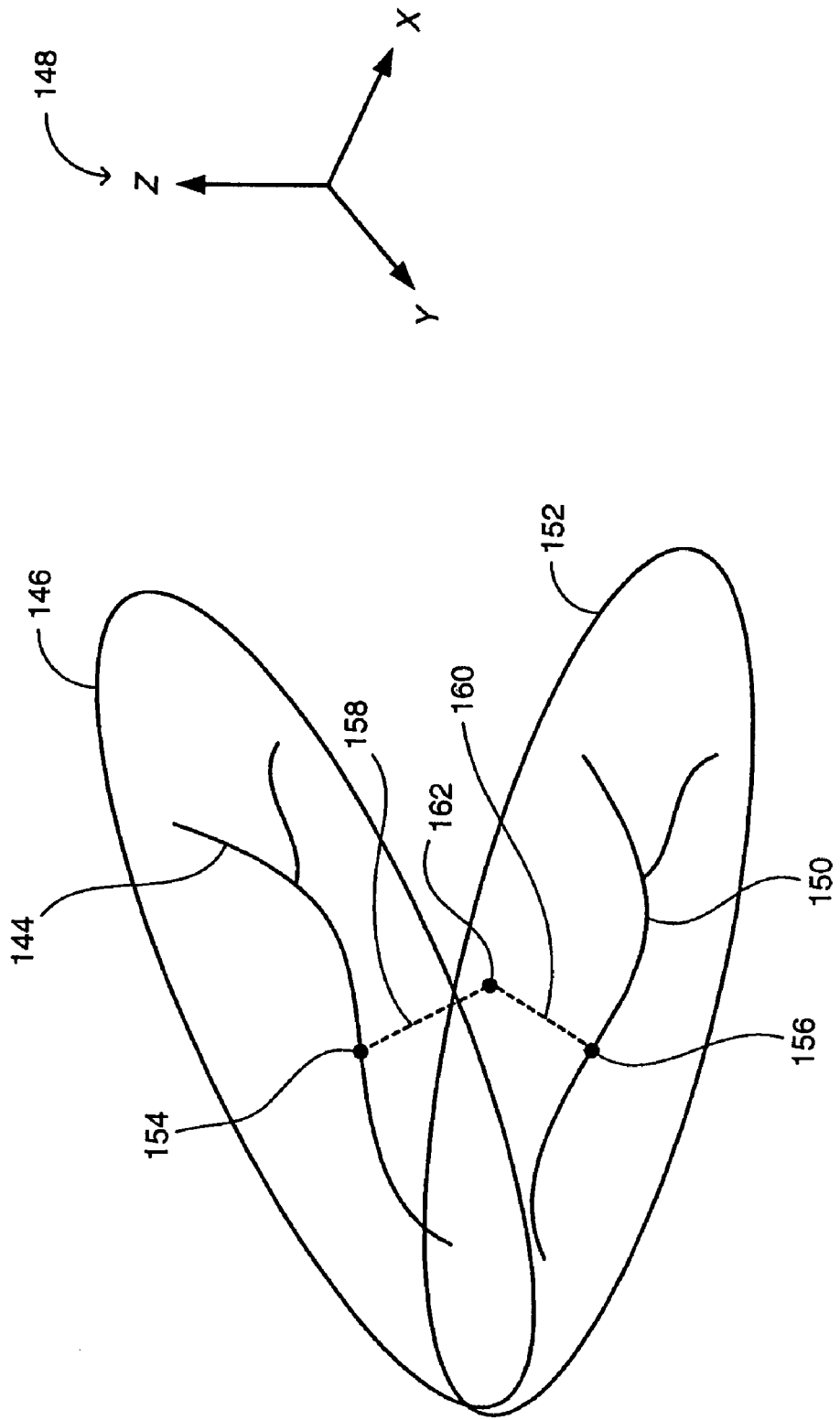
FIG. 2 is a schematic illustration of a method by which the imaging system of the system of FIG. 1 determines the coordinates of a path within the lumen, in three dimensions.

Reference is now made to FIGS. 1 and 2. FIG. 1 is a schematic illustration of a system, generally referenced 100, for automatically maneuvering a catheter within a lumen of the body of a patient, constructed and operative in accordance with an embodiment of the disclosed technique. FIG. 2 is a schematic illustration of a method by which the imaging system of the system of FIG. 1 determines the coordinates of a path within the lumen, in three dimensions.

With reference to FIG. 1, system 100 includes a joystick 102, a controller 104, a moving mechanism 106, a medical positioning system (MPS) 108, a plurality of transmitters 110A, 110B and 110C, an imaging system 112, a position detector 114, a catheter 116 and a display 118. Imaging system 112 includes a radiation generator 120 and a radiation detector 122. Imaging system 112 can be an X-ray system, fluoroscope, C-arm imager, computed tomography (CT), positron emission tomography (PET), ultrasound system, magnetic resonance imager (MRI), and the like.

Moving mechanism 106 can include a pair of angular movement rollers 124A and 124B, and a pair of linear movement rollers 126A and 126B, and respective moving elements (not shown) such as electric motors, actuators, and the like. However, moving mechanism 106 can include other, alternative or additional elements, as long as it imparts to catheter 116 the necessary motions described herein below (e.g., piezoelectric motors which transfer linear movement through friction). Optionally, moving mechanism 106 can be disposable in order to keep it sterile. Controller 104 includes a processor (not shown) and a storage unit (not shown) for storing information respective of a path 128, which catheter 116 should move according to, within a lumen 130 of the body (not shown) of a patient (not shown).

Moving mechanism 106 is coupled with joystick 102 and with controller 104. Controller 104 is coupled with imaging system 112. MPS 108 is coupled with controller 104 and with transmitters 110A, 110B and 110C. Position detector 114 is coupled with MPS 108 by a conductor 132 (i.e., a conductive coupling). Display 118 is coupled with MPS 108 and with imaging system 112. Position detector 114 is located at a distal portion of catheter 116.

During the medical operation, the body of the patient is located between radiation generator 120 and radiation detector 122. Imaging system 112 has at least one degree of freedom, thereby being able to take a plurality of images of the body of the patient, from different directions. Imaging system 112 provides a signal to display 118, respective of a two-dimensional image 134 of lumen 130, for display 118 to display two-dimensional image 134.

Path 128 is a three-dimensional curve between an origin 136 and a destination 138 of a distal portion (not shown) of catheter 116 relative to lumen 130. Both origin 136 and destination 138 are within a field of view of imaging system 112. Path 128 is determined during an imaging session prior to the medical operation, and stored in the storage unit.

Controller 104 calculates and constructs path 128, for example, according to a plurality of two-dimensional images obtained from lumen 130, with the aid of a C-arm imager. For example, the C-arm can obtain two two-dimensional ECG gated images of lumen 130 at two different non-parallel ECG gated image planes. When the user indicates origin 136 and destination 138, the C-arm constructs path 128 in three dimensions. It is noted that controller 104 calculates path 128 based on one or more image processing algorithms, according to contrast variations of lumen 130 relative to the background.

With further reference to FIG. 2, imaging system 112 captures an image 144 of lumen 130 on an image plane 146 in a three-dimensional coordinate system 148, and another image 150 of lumen 130 on an image plane 152 in three-dimensional coordinate system 148. Imaging system 112 is aware of the orientation between image planes 146 and 152 (i.e., the angles there between). Imaging system 112 identifies a feature 154 of lumen 130 in image 144 and a corresponding feature 156 in image 150. Imaging system 112 determines the three-dimensional coordinates of feature 154 (or feature 156) in three-dimensional coordinate system 148, by determining the intersection of normals 158 and 160 from features 154 and 156, respectively, to image planes 146 and 152, respectively, at a point 162. Imaging system 112 performs the above procedure for other features of lumen 130, thereby constructing path 128 in three dimensions.

A two-dimensional image which the C-arm obtains from the body of the patient, can include other lumens (not shown) in addition to lumen 130, which are located at planes different than the plane of lumen 130 (i.e., these additional lumens overlap lumen 130 in the captured image). In this case, when the user indicates origin 136 and destination 138, it is not evident to the C-arm that the user is interested in a path through lumen 130, and the C-arm can construct a path (not shown), which passes through another lumen which in the two-dimensional image overlaps lumen 130. Hence, the C-arm obtains another two-dimensional image of lumen 130 at another image plane, such that in the new two-dimensional image, lumen 130 is not overlapped by any other lumens.

Prior to the medical operation, the coordinate systems of MPS 108 and imaging system 112 are set to a common two-dimensional coordinate system, for display 118 to superimpose a representation 140 of position detector 114, on two-dimensional image 134, during the medical operation. This method is described for example, in U.S. patent application Ser. No. 09/949,160, which is incorporated herewith by reference. The information displayed by display 118, serves the physical staff to observe the location of the distal portion of catheter 116 relative to lumen 130, throughout the medical operation. This two-dimensional coordinate system can be determined for example, according to the following method.

A first transformation model between the three-dimensional coordinate system of MPS 108 and the three-dimensional coordinate system of imaging system 112 is determined. A second transformation model between the three-dimensional coordinate system of imaging system 112 and a two-dimensional coordinate system of imaging system 112 is determined. The three-dimensional coordinate system of MPS 108 is transformed to the three-dimensional coordinate system of imaging system 112, by applying the first transformation model to the three-dimensional coordinate system of MPS 108. The three-dimensional transformed coordinate system of imaging system 112 is transformed to the two-dimensional coordinate system of imaging system 112, by applying the second transformation model to the three-dimensional transformed coordinate system of imaging system 112.

The first transformation model is determined according to a set of points in the three-dimensional coordinate system of MPS 108 and another set of points in the three-dimensional coordinate system of imaging system 112. The second transformation model is determined according to external parameters of imaging system 112 (i.e., a set of points in the three-dimensional coordinate system of imaging system 112) and internal parameters of imaging system 112 (e.g., lens angle, focal length, magnification).

Following is a description of operation of system 100, for performing an operation on the vessels in the neck region of the patient. In this case, path 128 is a three-dimensional curve within the axillary artery (represented by lumen 130) which marks a path from the region of the first rib (i.e., origin 136) to the thyrocervical trunk (i.e., destination 138). At the stage of medical operation, the physical staff inserts catheter 116 to the body of the patient through the right brachial artery (not shown), and manually maneuvers catheter 116 to reach origin 136.

At this point, system 100 takes over, to automatically maneuver catheter 116 to destination 138. In response to the electromagnetic field produced by transmitters 110A, 110B and 110C, position detector 114 sends a signal to MPS 108 via conductor 132, respective of the three-dimensional position of position detector 114. Alternatively, position detector 114 is coupled with MPS 108 wirelessly and without conductor 132, in which case position detector 114 sends this position signal to MPS 108 wirelessly.

MPS 108 determines the coordinates of position detector 114 according to the signal received from position detector 114. MPS 108 sends a signal respective of the coordinates of position detector 114 to controller 104, in the three-dimensional coordinate system of MPS 108. MPS 108 sends a signal respective of the coordinates of position detector 114 to display 118, in the two-dimensional coordinate system of imaging system 112, as described herein above.

Throughout the medical operation, display 118 displays two-dimensional image 134 of an operational region of lumen 130 (i.e., a section between origin 136 and destination 138) according to a signal received from imaging system 112. Display 118 also displays representation 140 of the current location of position detector 114 (i.e., the distal portion of catheter 116), superposed on two-dimensional image 134, according to the signal received from MPS 108. Alternatively, the current location of the position detector can be superposed on a three-dimensional image of the lumen (e.g., the coronary tree).

Instead of path 128, the controller can employ a topographical representation of the lumen system of the patient, in order to control the moving mechanism to maneuver the catheter through the lumen system, from an origin to a destination within the lumen system. In this case, the controller determines the best path for the catheter to reach the destination. It is noted that the controller may change the path in real-time, depending on findings during the navigation process (e.g., blocked passages, lumen which is narrower than expected). The controller modifies the path according to the feedback provided in real time by the position detector, and by comparing the actual position and orientation of the position detector with the expected position and orientation. Furthermore, the controller modifies a predefined three-dimensional path which is used as a three-dimensional roadmap for the planning process.

The system can further include a processor (not shown) coupled with the MPS and with the display, and an organ monitor (not shown) such as an ECG coupled with the processor, as described in U.S. patent application Ser. No. 09/949,160. The organ monitor monitors the organ timing signal of a monitored organ and sends a respective signal to the processor. The processor sends a video signal to the display respective of an image of the lumen, corresponding with the current activity-state of the monitored organ detected by the organ monitor. The display displays an image of the lumen, according to the current activity-state. Thus, the display displays a superposition of a representation of the position detector on a reconstructed image of the lumen, taking into account the movements of the lumen due to the timing signal of the monitored organ (e.g., the heart beat of the patient). The display can display a three-dimensional reconstructed image of the lumen, as described in U.S. patent application Ser. No. 09/949,160. This three-dimensional reconstructed image is displayed relative to the coordinate system of the body of the patient.

Alternatively, the medical positioning system can filter out the organ timing signal (i.e., producing a filtered MPS reading) and the current position of the position detector in the coordinate system of the lumen, from a multitude of positions of the position detector, in the coordinate system of the body of the patient. In this case, the controller updates the topological representation and the position of the tip of the catheter according to the filtered MPS reading. The controller controls the moving mechanism according to the updated topological representation and the updated position of the catheter. Furthermore, the display can display the updated topological representation and the updated representation of the distal portion of the catheter, superposed on a substantially stationary three-dimensional reconstructed image of the lumen.

Moving mechanism 106 operates according to the commands received from controller 104, to maneuver catheter 116 along path 128, from origin 136 to destination 138. For this purpose, the pair of angular movement rollers 124A and 124B twist catheter 116 clockwise and counterclockwise relative to the longitudinal axis (not shown) of catheter 116, and the pair of linear movement rollers 126A and 126B move catheter 116 forward and backward. Controller 104 constantly receives a signal from MPS 108 respective of three-dimensional coordinates of position detector 114 at any given time (i.e., a feedback), thereby allowing moving mechanism 106 to apply corrections to possible errors of movement along path 128. These corrections are applied in the following manner.

Controller 104 sends a signal at predetermined time increments to moving mechanism 106, to advance catheter 116 by a predetermined displacement increment. Controller 104 determines the advancement of the distal portion of catheter 116 at each time increment (according to the position signal received from MPS 108), and checks whether this advancement substantially matches the predetermined displacement by which catheter 116 was supposed to advance. In case the actual detected advancement does not match the predetermined displacement increment, controller 104 determines that catheter 116 has made contact with an obstacle (not shown) which prevents catheter 116 to advance according to path 128 (e.g., the distal portion of catheter 116 can be stuck at a bifurcation 142).

In this case, controller 104 sends a signal to moving mechanism 106 to retreat catheter 116 by a selected increment backward within lumen 130, and also to twist the distal portion of catheter 116 by a selected amount. After this twist, controller 104 sends a signal to moving mechanism 106 to advance catheter 116 by a predetermined displacement increment. Thus, moving mechanism 106 can maneuver catheter 116 to overcome the obstacle and to enter the predetermined branch (in this case the thyrocervical trunk at bifurcation 142).

It is noted that due to the three-dimensional position information which controller 104 receives as a real time feedback from MPS 108, controller 104 can control the operation of moving mechanism 106 to maneuver catheter 116 in three-dimensions. Thus, system 100 provides an advantage over systems in the prior art, in which the physical staff can maneuver the catheter according to a two-dimensional display, only in two dimensions. System 100 provides automatic maneuvering of catheter 116 through lumen 130 in three dimensions, while performing feedback oriented real time corrections in order to reach destination 138 within lumen 130.

Imaging system 112 (e.g., a C-arm) can detect lumen 130 from different directions in order to provide the information necessary for display 118 to display two-dimensional image 134. Imaging system 112 selects the one specific imaging direction at which the average distance of path 128 from an image plane (not shown), is minimal. If $X_i$ is the distance from a point i on path 128 normal to the image plane, where i=1, 2, 3 . . . N, then the minimum average distance is, $$\min \frac{\sum_{1}^{N} X_i}{N} \quad (1)$$

In case path 128 follows many curves in space and deviates significantly from a two-dimensional path, then imaging system 112 can divide path 128 to different parts, and prepare the information for two-dimensional image 134, by selecting a different image plane for each part, while satisfying Equation 1.

It is noted that more than one position detector can be located at the distal portion of the catheter. This arrangement is crucial in case the distal portion of the catheter is provided with a "curve-back" functionality. The "curve-back" movement can be provided for example, by employing Electro Active Polymers (EAP). The moving mechanism is likewise provided with the necessary elements to apply an appropriate torque to the distal portion of the catheter, to bend the distal portion. Moreover, with the aid of multiple position detectors, the display can display the current geometry of the distal portion.

Furthermore, the controller can obtain a more complete information respective of the geometry of the distal portion of the catheter, when the catheter is blocked by an obstacle, and thus expedite the maneuvering operation. For example, if the controller detects that the distal portion of the catheter has unexpectedly bent, then the controller determines that the tip of the catheter has made contact with an obstacle in the lumen. The controller can reach this conclusion for example, by comparing the detected orientation of the position detector at a given point within the lumen, with the computed slope of the path at the same point within the lumen. In case the detected orientation and the computed slope do not match, the controller determines that the catheter has met an obstacle, thereby directing the moving mechanism to operate in order to move the catheter back from the obstacle.

In case the physical staff is unsatisfied with the automatic operation of moving mechanism 106, he can override controller 104, and manually operate moving mechanism 106 via joystick 102. The operator can intervene in any phase of operation of system 100, using joystick 102. This is a semiautomatic mode of operation of system 100, wherein controller 104 enables moving mechanism 106 to maneuver catheter 116 through the trivial portions of path 128, and the operator takes control of system 100 in the more intricate portions of path 128. In case of manual intervention, joystick 102 overcomes any automated action. Is noted that both in the automatic mode and the manual mode, the operator receives a visual feedback of the advancement of catheter 116 within lumen 130, by viewing representation 140 of the tip of catheter 116 on display 118.

Figure 3:
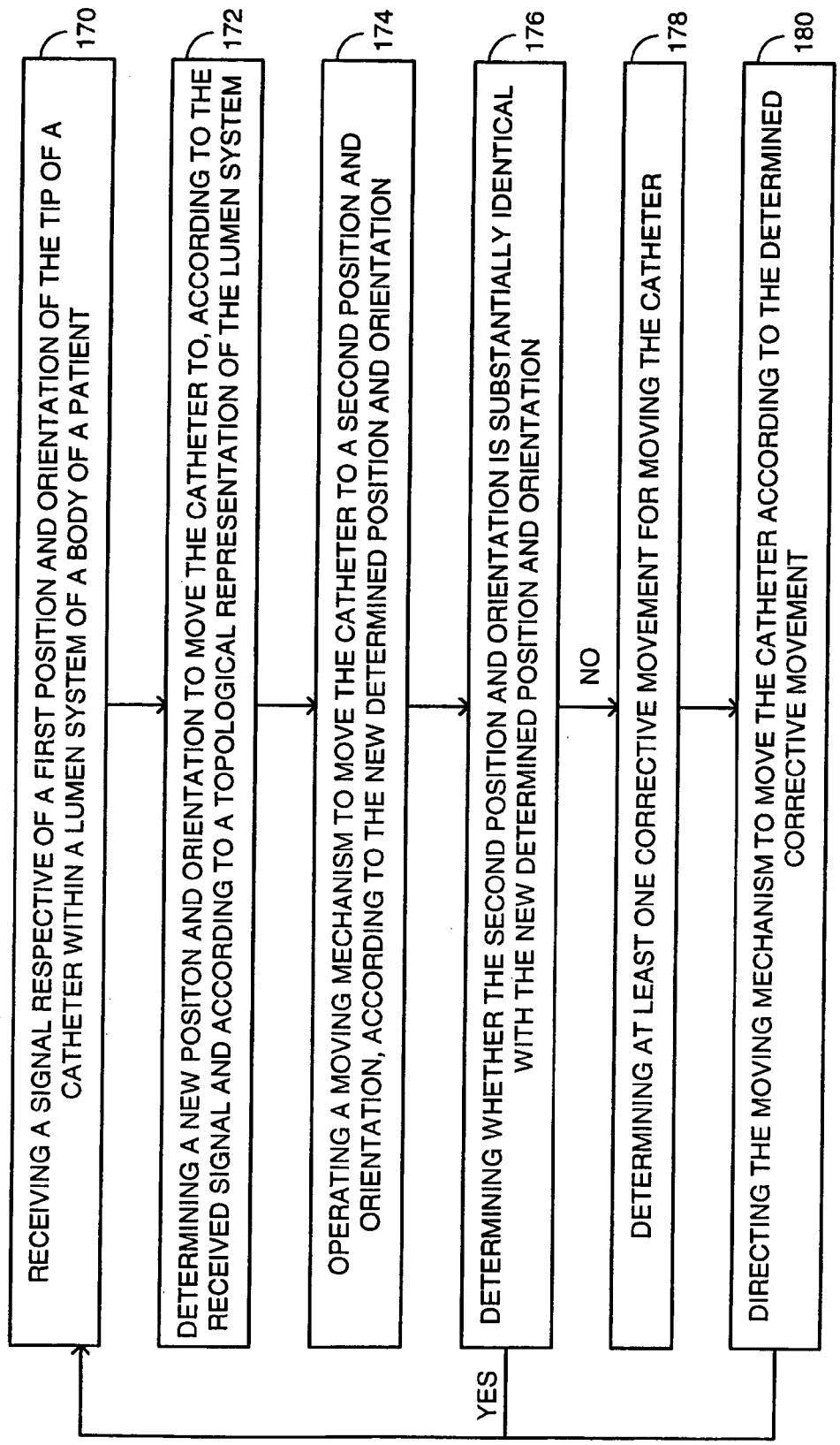
FIG. 3 is a schematic illustration of a method for operating the system of FIG. 1, operative in accordance with another embodiment of the disclosed technique.

Reference is now made to FIG. 3, which is a schematic illustration of a method for operating the system of FIG. 1, operative in accordance with another embodiment of the disclosed technique. In procedure 170, a signal respective of a first position of the tip of a catheter within a lumen system of a body of a patient is received. With reference to FIG. 1, controller 104 receives a signal from MPS 108 respective of the position of the distal portion of catheter 116, within lumen 130.

In procedure 172, a new position to move the catheter to, is determined according to the received signal and according to a topological representation of the lumen system. With reference to FIG. 1, controller 104 determines a new position for catheter 116 within lumen 130, according to the current position, and according to path 128.

In procedure 174, a moving mechanism is operated to move the catheter to a second position, according to the new determined position. With reference to FIG. 1, controller 104 sends a signal to moving mechanism 106 to move catheter 116 within lumen 130, to a second position, according to the new position determined in procedure 172, in order to advance catheter 116 within lumen 130 toward destination 138.

In procedure 176, it is determined whether the second position is substantially identical with the new determined position. If the outcome of the comparison is positive, then the method proceeds to procedure 170. Otherwise the method proceeds to procedure 178.

With reference to FIG. 1, controller 104 constantly receives a signal respective of the position of the tip of catheter 116 within lumen 130, and compares the current position with the position determined in procedure 172. If controller 104 determines that the current position is substantially identical with the one determined in procedure 172, then controller 104 determines that moving mechanism 106 has advanced catheter 116 as originally planned in procedure 172. In this case, procedures 170, 172 and 174 are repeated.

With reference to FIG. 1, controller 104 determines that the current position of the tip of catheter 116 is not identical with the one determined in procedure 172. Thus, controller 104 determines that catheter 116 has reached an obstacle, such as bifurcation 142, which prevents catheter 116 to advance within lumen 130 as planned in procedure 172.

In procedure 178, at least one corrective movement for moving the catheter is determined. With reference to FIG. 1, controller 104 for example, determines that catheter 116 has to be retreated within lumen 130 by a certain amount, twisted by a certain amount and then pushed forward within lumen 130, by a certain amount in order for catheter 116 to clear bifurcation 142.

In procedure 180, the moving mechanism is directed to move the catheter according to the determined corrective movement. With reference to FIG. 1, controller 104 for example, sends a signal to moving mechanism 106 for linear movement rollers 126A and 126B to pull catheter 116 by a selected linear increment within lumen 130, and for angular movement rollers 124A and 124B to twist the tip of catheter 116 by a selected amount. Controller 104 then sends a signal to moving mechanism 106 for linear movement rollers 126A and 126B to push catheter 116 by another selected linear increment. The method can then return back to procedure 170 to advance catheter 116 to another position toward destination 138 within lumen 130.

According to another aspect of the disclosed technique, the display is further coupled with the controller and with a pointing device, such as a mouse, tablet and stylus, cyber glove, joy stick, audio input device, and the like. A user defines a trail within the lumen system for the catheter to move along, by employing the pointing device. The controller directs the moving mechanism to move the catheter within the lumen along the defined trail, according to the entire topological representation of the lumen system. For this purpose, the controller continuously determines successive incremental paths from the current position of the catheter to a user defined position located in front of, and closest to the current position of the catheter.

At a bifurcation, the catheter can enter an adjacent lumen different than the one defined by the trail. In this case, the controller detects this deviation in course by detecting an unusually large difference between the current position of the tip of the catheter and the user defined position. The controller, then corrects the course by directing the moving mechanism to move the catheter back and advance it to the lumen marked by the trail.

Figure 4:
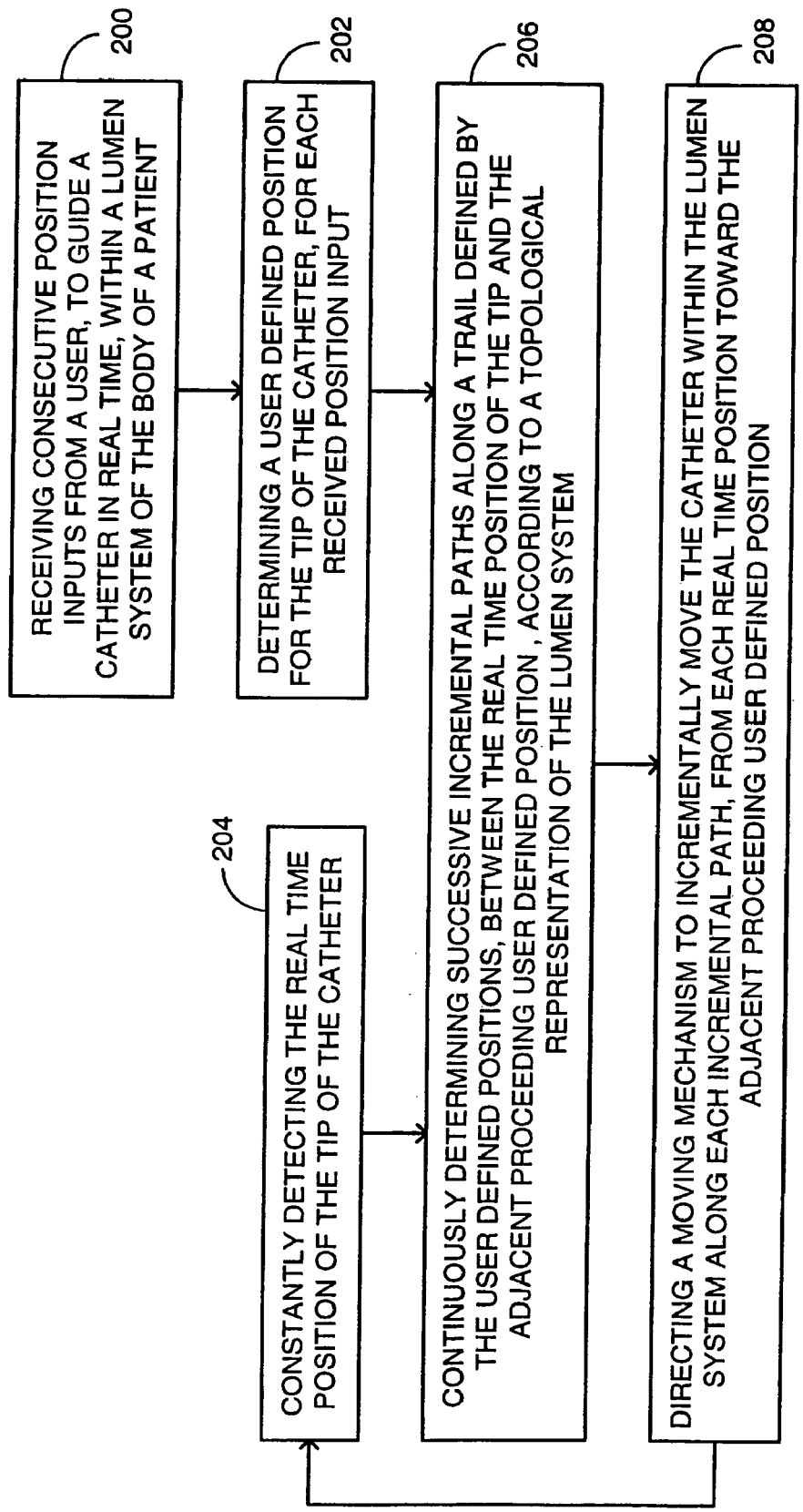
FIG. 4 is a schematic illustration of a method for operating the system of FIG. 1, operative in accordance with a further embodiment of the disclosed technique.

Reference is now made to FIG. 4, which is a schematic illustration of a method for operating the system of FIG. 1, operative in accordance with a further embodiment of the disclosed technique. In procedure 200, consecutive position inputs are received from a user, to guide a catheter in real time, within a lumen system of the body of a patient. With reference to FIG. 1, the user moves a cursor on display 118 along two-dimensional image 134 of lumen 130, thereby sending consecutive position inputs to controller 104 via the pointing device.

In procedure 202, a user defined position is determined for the tip of the catheter, for each received position input. With reference to FIG. 1, as the user moves the cursor and controller 104 receives position inputs from the pointing device, controller 104 determines a position for the tip of catheter 116 for each position input (i.e., the position of the cursor). A plurality of these positions define a trail in the lumen system.

In procedure 204, the real time position of the tip of the catheter is constantly detected. With reference to FIG. 1, position detector 114 of catheter 116 constantly detects the current position of the tip of catheter 116. MPS 108 determines this real time position and sends this information to controller 104. It is noted that procedures 200, 202 and 204 are performed simultaneously.

In procedure 206, successive incremental paths are continuously determined along a trail defined by the user defined positions, between the real time position of the tip of the catheter and the adjacent proceeding user defined position, according to a topological representation of the lumen system. Controller 104 determines a trail on the lumen system, according to the user defined positions which were determined in procedure 202. With reference to FIG. 1, controller 104 determines an incremental path between the current position of the tip of catheter 116 as detected by position detector 114, and a user defined position of the cursor located immediately in front of the current position of the tip of catheter 116. Controller 104 employs also the entire topological representation of the lumen system to determine each of the incremental paths.

In procedure 208, a moving mechanism is directed to incrementally move the catheter within the lumen system along each incremental path, from each real time position toward the adjacent proceeding user defined position. With reference to FIG. 1, controller 104 directs moving mechanism 106 to move catheter 116 incrementally within lumen 130, from the current position of the tip of catheter 116 as detected by position detector 114, to the user defined position located immediately in front of the current position of the tip of catheter 116.

Following procedure 208, the method returns to procedure 204, wherein a new incremental path is determined between a newly detected position of the tip of the catheter and the user defined position located immediately in front of the newly detected position of the tip of the catheter. Controller 104, then directs moving mechanism 106 to advance catheter 116 along the new incremental path. This cycle is continuously repeated, until the tip of catheter 116 reaches the last user defined position in the trail.

There can be a situation that at a bifurcation in the lumen system, catheter 116 enters an adjacent lumen not included in the trail. In this case, controller 104 detects that the tip of catheter 116 did not reach the user defined position which was supposed to reach. Controller 104 can detect this situation for example, by detecting that the tip of catheter 116 is outside a predetermined sphere around the user defined position. Controller 104 determines a corrective movement similar to the one described herein above in connection with procedures 178 and 180, except that controller 104 directs moving mechanism 106 to pull back catheter 116 from the incorrect lumen, and enter catheter 116 into the lumen which is indicated by the trail.

It will be appreciated by persons skilled in the art that the disclosed technique is not limited to what has been particularly shown and described hereinabove. Rather the scope of the disclosed technique is defined only by the claims, which follow.

The invention claimed is:

1. Method for guiding a catheter within a lumen system of the body of a patient, the method comprising the procedures of:
   receiving at least three consecutive position inputs from a user, to automatically guide said catheter, in real time, within said lumen system;
   determining, using a controller having a processor, a user defined position for the tip of said catheter, for each of said received consecutive position inputs, said user defined positions defining a trail for said catheter tip within said lumen system;
   constantly detecting, using a medical positioning system, the real time position of the tip of said catheter within said lumen system, based on a signal respective of the three-dimensional position of a position detector located at a distal portion of said catheter;
   determining continuously, using said controller having said processor, successive incremental paths along said trail each one of said incremental paths passing between said real time position and the adjacent proceeding user defined position, according to a topological representation of said lumen system, said topological representation being a three-dimensional mapping of said lumen system; and
   automatically directing a moving mechanism to incrementally move said catheter within said lumen system along each of said incremental paths, from each of a plurality of real time positions, toward said adjacent proceeding user defined position.

2. The method according to claim 1, wherein said procedure of receiving is performed according to movements of a pointing device.

3. The method according to claim 2 further comprising the step of selecting said pointing device from the group consisting of:
   mouse;
   tablet and stylus;
   audio input device;
   cyber glove; and
   joy stick.

4. The method according to claim 1, further comprising a procedure of automatically correcting the movement for said catheter, by said moving mechanism, when the tip of said catheter fails to reach said adjacent proceeding user defined position.

5. The method according to claim 4 wherein said automatically correcting step includes the sub-step of determining when the tip of said catheter enters an adjacent lumen not included in the trail.

6. The method according to claim 5 wherein said sub-step of determining when the tip of said catheter enters an adjacent lumen not included in the trail includes the further sub-step of detecting when the tip of said catheter is outside a predetermined sphere around one of the user defined positions.

7. The method according to claim 5 wherein said sub-step of determining when the tip of said catheter enters an adjacent lumen different than that defined by the trail includes the further sub-step of detecting an unusually large difference between a current position of the tip of the catheter and one of the user defined positions.

8. The method according to claim 4 wherein said automatically correcting step includes the sub-steps of (i) performing one of twisting and bending of said distal portion of said catheter and (ii) advancing said catheter in said lumen system.

9. Method for guiding a catheter within a lumen system of the body of a patient, the method comprising the steps of:
   receiving at least three consecutive position inputs from a user through movements by the user of a pointing device, to automatically guide said catheter, in real time, within said lumen system;
   determining, using a controller having a processor, a user defined position for the tip of said catheter, for each of said received consecutive position inputs, said user defined positions defining a trail for said catheter tip within said lumen system;
   constantly detecting, using a medical positioning system, the real time position of the tip of said catheter within said lumen system, based on a signal respective of the three-dimensional position of a position detector located at a distal portion of said catheter;
   determining continuously, using said controller having said processor, successive incremental paths along said trail each one of said incremental paths passing between said real time position and the adjacent proceeding user defined position, according to a topological representation of said lumen system, said topological representation being a three-dimensional mapping of said lumen system; and automatically directing a moving mechanism to incrementally move said catheter within said lumen system along each of said incremental paths, from each of a plurality of real time positions, toward said adjacent proceeding user defined position.

10. The method according to claim 9 further comprising the step of selecting said pointing device from the group consisting of:

mouse;
tablet and stylus;
audio input device;
cyber glove; and
joy stick.

11. The method of claim 9, further comprising a procedure of automatically correcting the movement for said catheter, by said moving mechanism, when the tip of said catheter fails to reach said adjacent proceeding user defined position.

12. The method of claim 11 wherein said automatically correcting step includes the sub-step of determining when the tip of said catheter enter an adjacent lumen not included in the trail.

13. The method of claim 12 wherein said sub-step of determining when the tip of said catheter enters an adjacent lumen not included in the trail includes the further sub-step of detecting when the tip of said catheter is outside a predetermined sphere around one of the user defined positions.

14. The method of claim 12 wherein said sub-step of determining when the tip of said catheter enters an adjacent lumen different than that defined by the trail includes the further sub-step of detecting an unusually large difference between a current position of the tip of the catheter and one of the user defined positions.

15. The method of claim 11 wherein said automatically correcting step includes the sub-steps of (i) performing one of twisting and bending of said distal portion of said catheter and (ii) advancing said catheter in said lumen system.

* * * * *